United States Patent
Egger

(10) Patent No.: US 6,350,610 B2
(45) Date of Patent: Feb. 26, 2002

(54) APPARATUS FOR MEASURING A MIGRATION ABILITY OF AMEBOIDALLY MOBILE CELLS

(76) Inventor: Gerd Egger, Sonnenstrasse 4, A-8010 Graz (AT)

( * ) Notice: Subject to any disclaimer, the term of this patent is extended or adjusted under 35 U.S.C. 154(b) by 0 days.

(21) Appl. No.: 09/770,713

(22) Filed: Jan. 25, 2001

Related U.S. Application Data

(63) Continuation of application No. PCT/AT99/00165, filed on Jun. 24, 1999.

(30) Foreign Application Priority Data

Sep. 22, 1998 (AT) ................................................ 1854/98

(51) Int. Cl.⁷ .............................................. C12M 1/34
(52) U.S. Cl. ................. 435/287.1; 435/287.7; 435/287.8; 435/287.9; 435/297.5
(58) Field of Search ........................... 435/287.1, 287.7, 435/287.8, 287.9, 288.3, 288.4, 295.5, 797.1, 305.1, 305.2, 810

(56) References Cited

U.S. PATENT DOCUMENTS

| | | | | |
|---|---|---|---|---|
| 2,923,669 A | * | 2/1960 | Poitras | |
| 4,693,834 A | * | 9/1987 | Hossom | |
| 5,081,017 A | * | 1/1992 | Longoria | |
| 5,135,872 A | * | 8/1992 | Pouletty et al. | |
| 5,141,718 A | * | 8/1992 | Clark | |
| 5,403,741 A | * | 4/1995 | Holbrook | |

FOREIGN PATENT DOCUMENTS

| | | | |
|---|---|---|---|
| EP | 0 334 015 A2 | * | 9/1989 |
| WO | WO-00/17652 A1 | * | 3/2000 |

\* cited by examiner

*Primary Examiner*—William H. Beisner
(74) *Attorney, Agent, or Firm*—Herbert L. Lerner; Laurence A. Greenberg; Werner H. Stemer

(57) ABSTRACT

An apparatus for measuring the ability of ameboidally mobile cells to migrate has a deposit of active substance in the form of a plate, a membrane filter disposed on the deposit and one or more vessels on the filter. The vessel or vessels have a base opening, for a liquid which contains ameboidally mobile cells. The base opening in the vessel bears against the membrane filter. A surface area of the membrane filter is at least 1.6 times as large as the area of the base opening in the vessel.

12 Claims, 1 Drawing Sheet

APPARATUS FOR MEASURING A MIGRATION ABILITY OF AMEBOIDALLY MOBILE CELLS

CROSS-REFERENCE TO RELATED APPLICATION

This is a continuation of copending International Application PCT/AT99/00165, filed Jun. 24, 1999, which designated the United States.

BACKGROUND OF THE INVENTION

Field of the Invention

The present invention relates to an apparatus for measuring the ability of ameboidally mobile cells to migrate. The apparatus comprises a deposit of active substance in the form of a plate, a membrane filter disposed above the deposit, and at least one vessel, which is arranged on top of the filter and has a base-side opening. The base-side opening in the vessel bears against the membrane filter.

Active substances are understood as meaning all substances which promote or inhibit the migration of ameboidally mobile cells.

Since the ability of ameboidally mobile cells to migrate is an essential characteristic of such cells, it is of considerable interest to theoretical and applied medicine. With regard to the importance of measuring the ability of ameboidally mobile cells to migrate, its application in human medicine and with regard to an apparatus according to the prior art, reference is had to the disclosure in my prior Austrian patent No. AT 394455 B, which is herewith incorporated by reference.

SUMMARY OF THE INVENTION

The object of the invention is to provide an apparatus for measuring the ability of ameboidally mobile cells to migrate which overcomes the above-noted deficiencies and disadvantages of the prior art devices and methods of this kind, and wherein, on the one hand, the efficiency of the apparatus and its measurement accuracy are increased and, on the other hand, the measurement method is considerably simplified, and the way in which it is carried out is considerably accelerated, thus making it easier to carry out series of measurements.

With the above and other objects in view there is provided, in accordance with the invention, an apparatus for measuring an ability of ameboidally mobile cells to migrate, comprising:

a plate-shaped deposit of active substance;

a membrane filter disposed on the deposit; a vessel disposed on the membrane filter, the vessel having a base formed with a base-side opening for a liquid containing ameboidally mobile cells, the base-side opening in the vessel bearing against the membrane filter; the membrane filter having a surface area at least 1.6 times as large as an area of the base-side opening; adhesive areas disposed to connect the deposit of active substance and the membrane filter, the adhesive areas amounting at most to substantially 30% of an area over which the deposit of active substance and the membrane filter bear against one another.

In other words, the area of the membrane filter is at least 1.6 times as great as the area of the base opening of the vessel. Preferably, the deposit of active substance and the membrane filter are joined to one another adhesively such that individual areas of adhesive which extend over their surfaces which bear against one another, preferably arranged in the form of a grid, amount to at most 30% of the area of those surfaces of the deposit of active substance and of the membrane filter which bear against one another. An device of this nature ensures close contact between the deposit of active substance and the membrane filter while simultaneously allowing liquids and substances dissolved therein to pass through between the deposit of active substance and the membrane filter.

In accordance with an added feature of the invention, the deposit of active substance, the membrane filter and the vessel are placed on top of a support plate made of a transparent or translucent material, and the deposit of active substance and the membrane filter are made from a transparent material or a material which can be changed into a transparent state. This makes it possible to evaluate the ability of the cells to migrate using a microscopic transillumination method, i.e., by transmitted light.

In order to further facilitate large series of measurements, it is possible for individual measurement devices which, for example, contain different active substances to be combined to form a measurement unit, in which case a multiplicity of the measurement devices may be provided, in order to increase accuracy. For this purpose, the membrane filter is preferably designed as an at least approximately rectangular plate, to the underside of which a plurality of deposits of active substance are attached, in particular by adhesive bonding, and on which a plurality of vessels for the cells to be analyzed are arrayed, each vessel being assigned its own deposit of active substance. It is possible for the vessels to be arrayed in adjacent rows, the vessels in one row being connected to one another by webs or the like to form units.

In accordance with a concomitant feature of the invention, the vessels may be connected to the membrane filter, once again by adhesive bonding. This adhesive bonding is preferably formed in such a way that, after the process of migration has ended, it can easily be detached from the membrane filter without damaging the latter. Preferably, the deposits of active substance, the membrane filter and the vessels situated thereon are placed onto an elongate support plate made from a transparent or translucent material, and the deposits of active substance and the membrane filter are made from a transparent material or from a material which can be changed into a transparent state.

Other features which are considered as characteristic for the invention are set forth in the appended claims.

Although the invention is illustrated and described herein as embodied in an apparatus for measuring the ability of ameboidally mobile cells to migrate, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
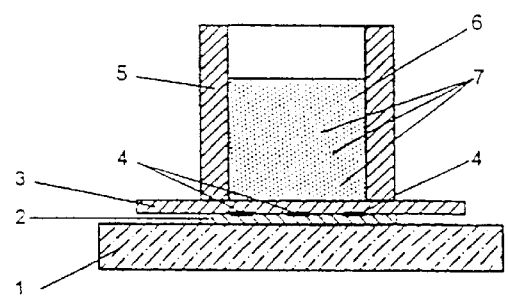
FIG. 1 is a diagrammatic vertical section of a first embodiment of an apparatus according to the invention.

Referring now to the figures of the drawing in detail and first, particularly, to FIG. 1 thereof, there is seen a support plate 1 on which there is a deposit of active substance 2. Above the deposit of active substance 2 there is a membrane filter 3 which is joined to the deposit of active substance 2 via a plurality of adhesive bonds 4. Above the membrane filter 3 there is a tubular vessel 5, into which a liquid 6 has been introduced which contains cells 7 whose ability to migrate is to be measured. The membrane filter 3 has an area which is equal to at least 1.6 times the size of the base opening of the vessel 5.

The membrane filter 3 exerts suction on the liquid 6 together with the cells 7 contained therein. As a result, liquid also passes into the deposit of active substance 2 which is arranged beneath the membrane filter 3, during which process portions of the active substance are dissolved and subsequently diffuse into the membrane filter 3 and the liquid above it. As a result, the cells 7 are acted on in such a way that their migration into the membrane filter 3 is influenced.

The fact that the area of the membrane filter 3 is at least 1.6 times as large as the base opening in the vessel 5 leads to a significantly stronger suction being exerted on the liquid 6, together with the cells 7 contained therein, situated in the vessel 5 than would be the case if the membrane filter is of approximately the same size as the base opening of the vessel 5. As a result, the cells 7 are brought into contact with the membrane filter 3 more quickly and can penetrate into this filter more rapidly, so that the time required for the measurement is reduced.

Since the ability of some types of cell to migrate may change rapidly outside the organism, a reduced measurement time leads to an improved determination of the diagnostically significant original readiness of the cells to migrate. Therefore, the increased suction provided by the enlarged membrane filter results in significantly more accurate measurement results as compared to the known prior art.

The fact that the deposit of active substance 2 is joined to the membrane filter 3 by adhesive bonding so as to bear tightly against it ensures that the active substance is dissolved and then diffuses into the membrane filter 3 and onward into the liquid 6 inside the vessel 5 in a controlled, uniform manner, which is one of the preconditions for the reproducibility and standardization of migration measurements. However, the total area of the bonded surfaces 4 should cover no more than 30% of the surfaces bearing against one another, since otherwise the diffusion of the liquid into the deposit of active substance 2 and, in addition, the diffusion of the dissolved active substance out of the deposit of active substance 2 into the membrane filter 3 would be considerably restricted. The individual bonded areas 4 may be arrayed in a grid-like pattern.

After the migration process has ended, the cells which have migrated into the membrane filter 3 are made visible, for example by staining, and then their number, distribution, and shape are determined by means of a microscopic assessment method. If the components of the apparatus are transparent or can be made transparent, an illumination method by transmitted light, i.e., transillumination, can be employed for this purpose.

Figure 2:
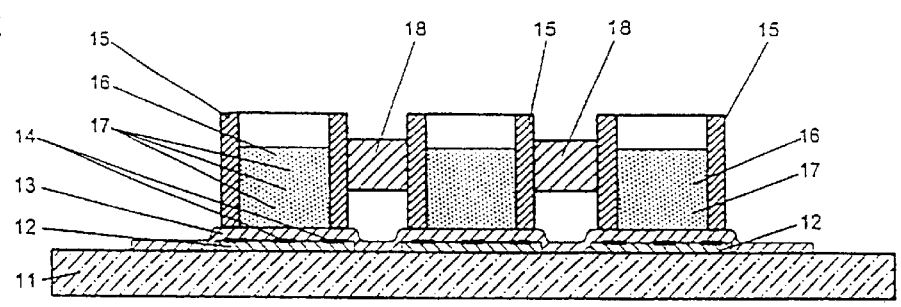
FIG. 2 is a vertical section taken along the line II—II in FIG. 3, and illustrating a second embodiment of an apparatus according to the invention which represents a measurement unit and makes it easier to carry out large series of measurements.
Figure 3:
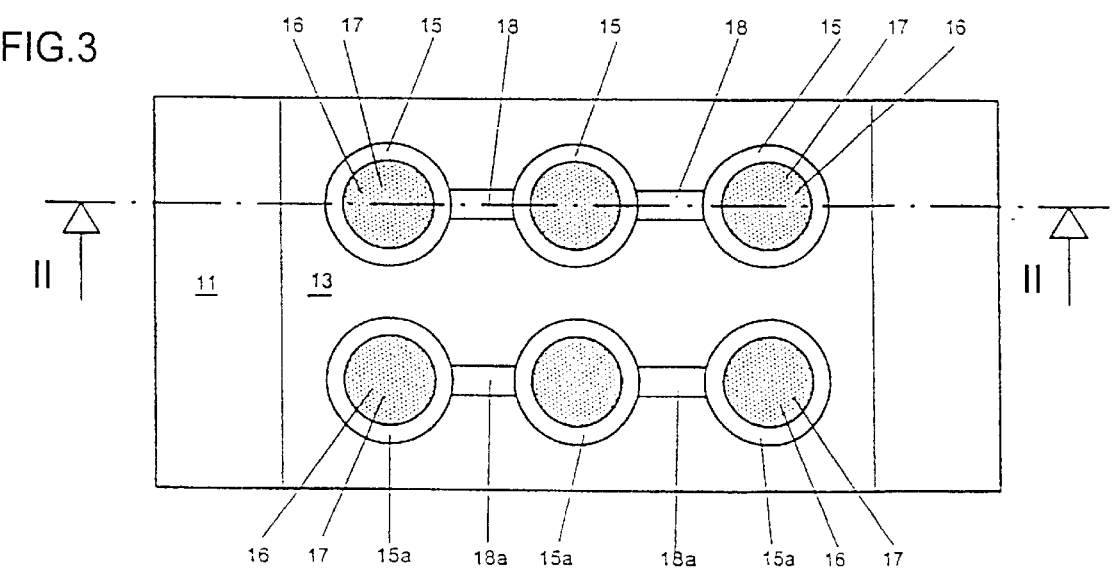
FIG. 3 is a plan view of the apparatus of FIG. 2.

The basic structure and fundamental function of an apparatus of this type have been described with reference to FIG. 1. By contrast, FIGS. 2 and 3 illustrate an apparatus of this type which can be used to facilitate series of measurements. In this apparatus, a plurality of the components illustrated in FIG. 1 are combined to form one measurement unit, allowing a simple, rapid and clear migration measurement to be carried out.

The second embodiment of the apparatus comprises a rectangular support plate 11 which is preferably made from a transparent or translucent material. A mat-like membrane filter 13, which covers a plurality of deposits of active substance 12 which are spaced apart from one another, is situated on top of this support plate 11. The deposits of active substance 12 are joined to the membrane filter 13 by means of a plurality of adhesive bonds. The deposits of active substance 12 and those parts of the membrane filter 13 which do not cover the deposits of active substance 12 are also joined to the support plate 11 by adhesive bonds.

In this exemplary embodiment, two rows of three vessels 15 and 15a each, into which the liquid 16 containing the cells 17 to be analyzed has been introduced, are situated above the membrane filter 13. The individual vessels 15 and 15a in the two rows are connected to one another by means of webs 18 and 18a to form units. As a result, during production of the apparatus they can be placed onto the membrane filter 13 together and then adhesively bonded to the filter. In addition, they can be detached from the membrane filter 13 together after the migration process and the preparation of the cells which have migrated into the membrane filter 13. The deposits of active substance 12 situated beneath the three vessels 15 are laden with an active substance, whereas the deposits of active substance situated beneath the vessels 15a arranged parallel to the vessels 15 do not contain any active substance, since they are used to measure the unstimulated, spontaneous cell migration. The measurement which is carried out in triplicate simultaneously in the exemplary embodiment is used to increase the measurement accuracy.

According to another exemplary embodiment, the deposits of active substance 12 beneath the vessels 15 and 15a are each laden with different active substances, so that it is possible to compare the different effects of these substances on the migration of the cells which are to be analyzed.

According to another method, after the migration process has concluded, the cells which have migrated into the membrane filter 13 are fixed and stained as a result of suitable substances being added to the vessels 15 and 15a. After preparation has been finished, the vessels 15 and 15a are detached from the membrane filter 13. The cells which have migrated into the membrane filter 13 are then accessible for microscopic analysis.

In one exemplary embodiment, the vessels 15 and 15a have an internal diameter of approximately 7 mm and a height of approximately 9 mm. The membrane filter 13 and the deposits of active substance 12 are each 140 $\mu$m thick. The vessels 15 and 15a and the support plate 11 can be made of plastic or of glass. The only required criterion is that they be inert with respect to the media used and the cells to be analyzed.

I claim:

1. An apparatus for measuring an ability of ameboidally mobile cells to migrate, comprising:
   a plate-shaped deposit of active substance;
   a membrane filter disposed on said deposit;
   a vessel disposed on said membrane filter, said vessel having a base formed with a base-side opening for a liquid containing ameboidally mobile cells, said base-side opening in said vessel bearing against said membrane filter;

said membrane filter having a surface area at least 1.6 times as large as an area of said base-side opening;

adhesive areas disposed to connect said deposit of active substance and said membrane filter, said adhesive areas amounting at most to substantially 30% of an area over which said deposit of active substance and said membrane filter bear against one another.

2. The apparatus according to claim 1, wherein said adhesive areas are a plurality of adhesive areas arranged in form of a grid.

3. The apparatus according to claim 1, wherein the area of said deposit of active substance is approximately equal to a base area of said vessel.

4. The apparatus according to claim 1, which comprises a support plate of translucent material carrying said deposit of active substance, said membrane filter, and said vessel, and wherein said deposit of active substance and said membrane filter are made of a transparent material or a material capable of changing into a transparent state.

5. The apparatus according to claim 4, wherein said support plate is formed of transparent material.

6. The apparatus according to claim 1, wherein said membrane filter is an at least substantially rectangular plate having an underside with plurality of said deposits of active substance attached thereto, and a top carrying a plurality of vessels arranged in groups of mutually interconnected vessels.

7. The apparatus according to claim 6, which comprises webs interconnecting said vessels to form units.

8. The apparatus according to claim 6, wherein said deposits of active substance are adhesively bonded to said underside of said plate.

9. The apparatus according to claim 6, wherein said vessels are arranged in mutually adjacent rows, and said vessels of each row are connected to one another to form units.

10. The apparatus according to claim 6, wherein said vessels are adhesively bonded to said membrane filter.

11. The apparatus according to claim 6, which comprises an elongate support plate of translucent material carrying said deposits of active substance, said membrane filter, and said vessels, and wherein said deposits of active material and said membrane filter are made of a transparent material or a material capable of changing into a transparent state.

12. The apparatus according to claim 11, wherein said support plate is formed of transparent material.

* * * * *